(12) United States Patent
Cover et al.

(10) Patent No.: US 8,526,341 B2
(45) Date of Patent: Sep. 3, 2013

(54) SYSTEMS AND METHODS FOR MICROWAVE TOMOGRAPHY

(75) Inventors: Mathew B. Cover, Iowa City, IA (US); David R. Andersen, Coralville, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 320 days.

(21) Appl. No.: 12/123,346

(22) Filed: May 19, 2008

(65) Prior Publication Data
US 2009/0040952 A1 Feb. 12, 2009

Related U.S. Application Data

(60) Provisional application No. 60/930,823, filed on May 17, 2007.

(51) Int. Cl.
*H04B 7/00* (2006.01)

(52) U.S. Cl.
USPC ........................................................ 370/310

(58) Field of Classification Search
USPC .............. 370/310, 252, 253; 455/446, 456.5, 455/456.1; 367/7
See application file for complete search history.

(56) References Cited

U.S. PATENT DOCUMENTS

| | | | | |
|---|---|---|---|---|
| 6,745,038 B2* | 6/2004 | Callaway et al. | ........... | 455/456.1 |
| 7,099,676 B2* | 8/2006 | Law et al. | ................... | 455/456.6 |
| 7,457,378 B1* | 11/2008 | Sher et al. | ...................... | 375/345 |
| 2001/0022558 A1* | 9/2001 | Karr et al. | ...................... | 342/450 |
| 2004/0070582 A1* | 4/2004 | Smith et al. | .................... | 345/419 |
| 2006/0019679 A1* | 1/2006 | Rappaport et al. | .......... | 455/456.5 |
| 2007/0035437 A1* | 2/2007 | Steinway et al. | ................ | 342/22 |
| 2007/0099622 A1* | 5/2007 | Rappaport et al. | ............ | 455/446 |

OTHER PUBLICATIONS

"Microwave tomography using dynamic 802.15.4 wireless networks" Cover, M.B. ; Kanukurthy, K.S. ; Andersen, D.R. ; Univ. of Iowa, Iowa City This paper appears in: Electro/Information Technology, 2007 IEEE International Conference on Issue Date : May 17-20, 2007 On pp. 251-256 Location: Chicago, IL Print ISBN: 978-1-4244-0941-9 INSPEC.* http://en.wikipedia.org/wiki/Tomography This page was last modified on Aug. 10, 2010 at 22:55.*

* cited by examiner

*Primary Examiner* — Gary Mui
(74) *Attorney, Agent, or Firm* — Schwegman Lundberg & Woessner, P.A.

(57) ABSTRACT

Systems and methods for microwave tomography are described. According to various embodiments, signal strength values or other similar quality indications may be analyzed as they are received with packet data over a wireless network. The analysis may be used to determine the presence of a physical object substantially between communicating nodes in the wireless network. An output may be generated based on analyzed data. Other embodiments are described and claimed.

19 Claims, 10 Drawing Sheets

SYSTEMS AND METHODS FOR MICROWAVE TOMOGRAPHY

RELATED APPLICATION

This application claims the benefit of U.S. Provisional Application Ser. No. 60/930,823 filed May 17, 2007, which is incorporated herein and made a part hereof in its entirety.

STATEMENT OF GOVERNMENT RIGHTS

This invention was made with a grant from the Government of the United States of America (Grant No. DK64659 from The National Institutes of Health). The Government has certain rights in the invention.

BACKGROUND

Tomography has revolutionized the way medical imaging has been done over the last few decades. The development of efficient and flexible wireless sensor networks creates wide variety of potentially new imaging modalities. One example technology is the IEEE 802.15.4 specification which provides the framework for an efficient wireless network. IEEE 802.15.4 emphasizes energy efficiency, flexibility and low cost of personal area networks (PAN) in sending data from one location to another. This and other wireless networks are designed and used for communication and analysis of data located in the payload of packets.

BRIEF DESCRIPTION OF THE DRAWINGS

Embodiments of inventive subject matter may be best understood by referring to the following description and accompanying drawings, which illustrate such embodiments. In the drawings.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

Figure 1:
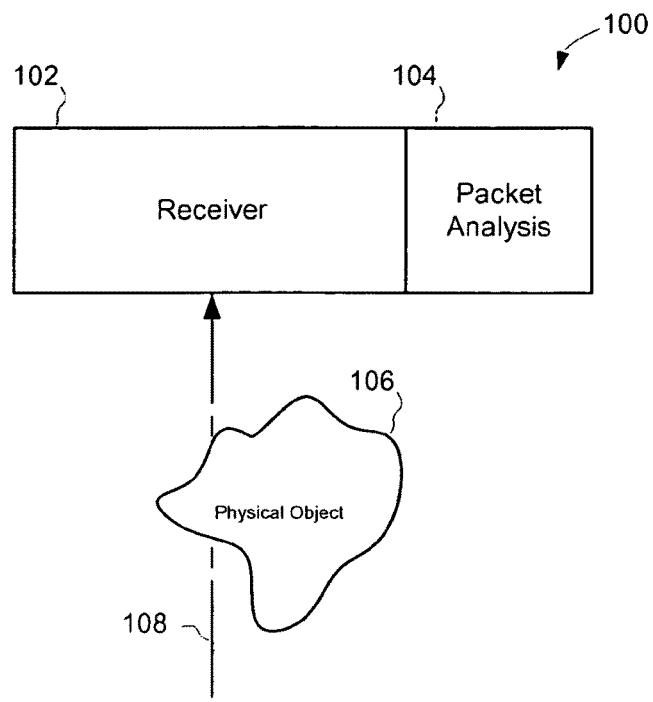
FIG. 1 is a block diagram of a wireless device for microwave tomography according to various embodiments.

FIG. 1 is a block diagram of a wireless device 100 for microwave tomography according to various embodiments. The wireless device 100 includes a receiver 102, and a packet analysis module 104. The receiver 102 receives a packet over a wireless path 108. The packet may include non-payload data which may be analyzed by the packet analysis module 104. The term packet refers to any block of data that may be over a network which may include identities of sending and receiving nodes, and may be capable of carrying a payload. The non-payload data may include packet identifying data, source identification data, signal strength data and signal quality data, among other characteristic data. The non-payload data may be analyzed to determine the presence of a physical object 106 along the wireless path 108. The wireless path may represent the straight-line path from a packet source to the receiver 102.

The determination of a physical object 106 along the wireless path 108 may be done within the wireless device 100, the packet analysis module 104, or on an external computer or processor.

Figure 2:
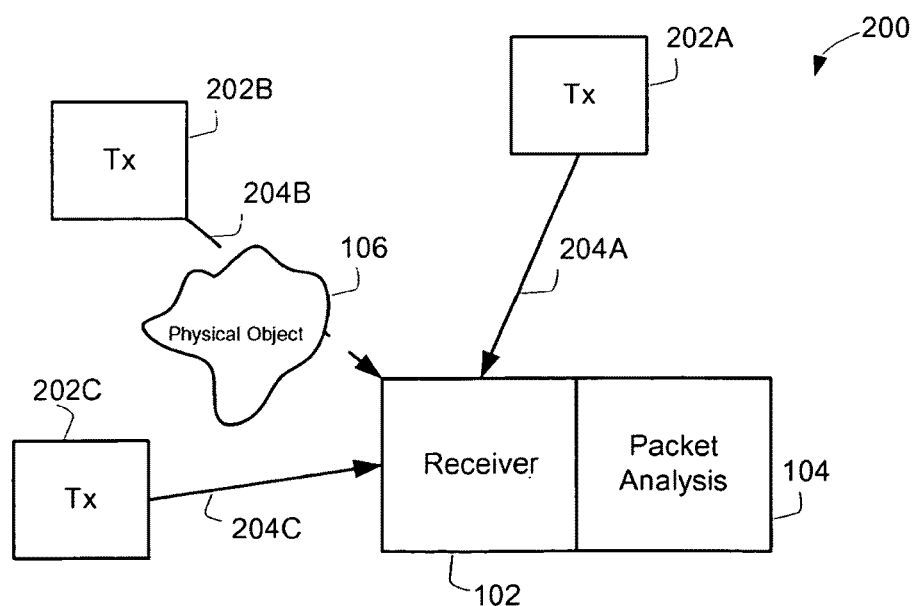
FIG. 2 is a block diagram of a system for microwave tomography according to various embodiments.

FIG. 2 is a block diagram of a system 200 for microwave tomography according to various embodiments. The system 200 includes the receiver 102, the packet analysis module 104, the physical object 106, wireless transmitters 202A-202C and associated wireless paths 204A-204C. Similar to as described above with respect to FIG. 1, the receiver 102 may receive packets from transmitters 202A-C. Non-payload information from the packets may be analyzed by the packet analysis module 104. Using the non-payload information included with the packets from each transmitter 202A-C, a tomographic analysis may be completed to take into account relative locations of the transmitters 202A-C, as well as signal strength and quality information. This analysis may be used to determine of the presence of a physical object 106 along a wireless path 204A-C. Additionally, the analysis may provide a spatial representation of the location and size of the physical object 106. A tomographic analysis application may be used to compile the non-payload information from a number of packets (and transmitters 202A-C) into data representing the position, size, shape, or other characteristics of the physical object 106. This data may be in textual form or in image form as a tomogram.

Figure 3:
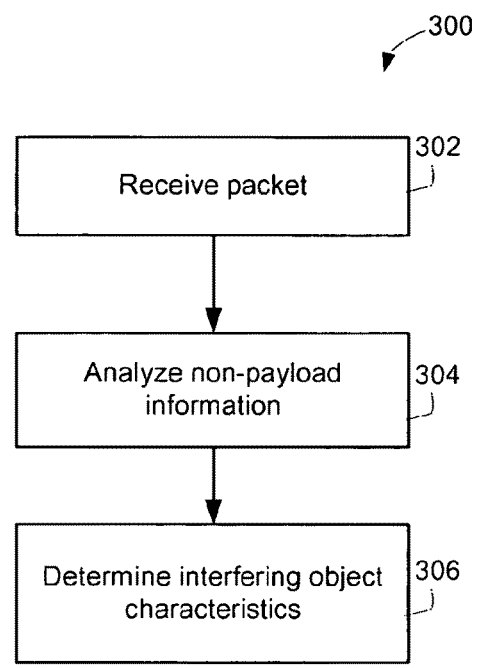
FIG. 3 is a flow diagram illustrating a method for performing microwave tomography according to various embodiments.

FIG. 3 is a flow diagram illustrating a method 300 for performing microwave tomography according to various embodiments. The method 300 begins by receiving a packet (block 302). The packet may contain data, or it may have zero payload. The information not included in the payload of the packet may be analyzed (block 304). This information may include the source of the packet, signal quality and/or signal strength information. Data may be available to determine a relative location of the source of the packet. Using source location data and signal quality/strength data, a determination may be made regarding characteristics of interfering objects. An interfering object may be an object substantially along a straight-line path from the packet source to the packet receiver. The interfering object characteristics may include location, size, movement, reflectivity, and other characteristics.

By using non-payload data such as the received signal strength indication (RSSI) value of packets being received in the network with a known physical configuration, deflections in the RSSI value may indicate a physical obstruction in the network. In this way, the wireless network itself may be used as a dynamic sensor to collect data. A tomography application of a much larger scale than medical applications can be deployed on the scale of rooms, or larger depending on the wireless air interface used. The 802.15.4 direct sequence spread spectrum (DSSS) radios provide a means of filtering out noise. These radios are less susceptible to interference as they spread the signal over a band and also allow sharing of a single channel among many users.

In much the same way that a CT scan is done in a hospital to get a cross-sectional image of a human, a wireless data network can be used to obtain a cross-sectional image of a coverage area. Phantom objects may be discovered and identified by analyzing signal strength or quality values of transmitted packets. The ZigBee network protocol, for example, could be exploited for its ad hoc ability to autonomously create networks. In an embodiment, every remote node can be programmed with the exact same code and the network will configure itself. The number of nodes that can connect to the network is really practically limited by the amount of memory in a coordinator node. Possible applications include monitoring of fields, determining the contents of enclosed buildings/structures, security systems, and entertainment at venues.

The IEEE 802.15.4 standard is used as an example wireless system, but the present subject matter should not be taken to be limited to any particular wireless protocol or air interface. The previous and following examples which may be focused on 802.15.4 technology may include details which are specific to 802.15.4; however, it should be clear to one skilled in the art that the ideas may be equivalently applied to other wireless technologies as well.

The IEEE 802.15.4 standard was first approved in May 2003 to define a standard that would "provide a standard for ultra-low complexity, ultra-low cost, ultra-low power consumption, and low data rate wireless connectivity among inexpensive devices." (IEEE std. 802.15.4-2003: Wireless Medium Access Control (MAC) and Physical Layer (PHY) specifications for Low Rate Wireless Personal Area Networks (LR_WPANs)

The 802.15.4 standard primarily outlines the PHY and MAC layers, but offers much in terms of guidelines for network layers and possible software architectures. The data rate for 802.15.4 varies depending on what range of frequencies a device is operating on. For the 2.4 GHz band, the raw data rate is 250 kb/s, 915 MHz data rate is 40 kb/s, and 868 MHz is 20 kb/s.

The 802.15.4 standard defines two types of devices that can participate in a network: a full-function device (FFD) and reduced-function devices (RFD). FFDs can serve as personal area network (PAN) coordinators. A reduced-function device (RFDs) is a device with a minimal implementation of the IEEE 802.15.4 protocol. The standard only allows RFDs to communicate with FFDs. The 802.15.4 specification defines two types of topologies of networks that can be formed using the standard: star and peer-to-peer. Both types require at least one FFD to serve as the PAN coordinator.

Figure 4A:
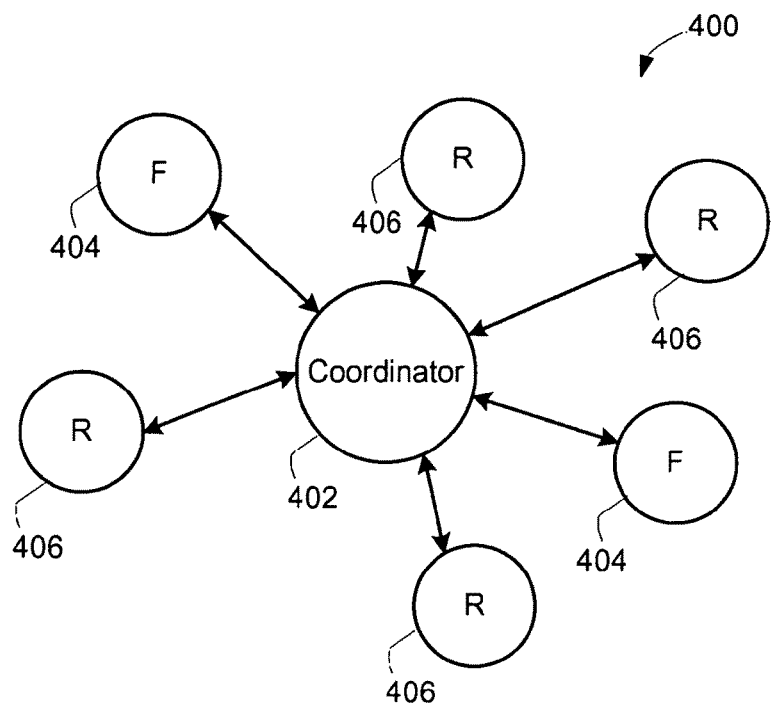
FIGS. 4A and 4B are block diagrams of wireless networks for microwave tomography according to example embodiments.
Figure 4B:
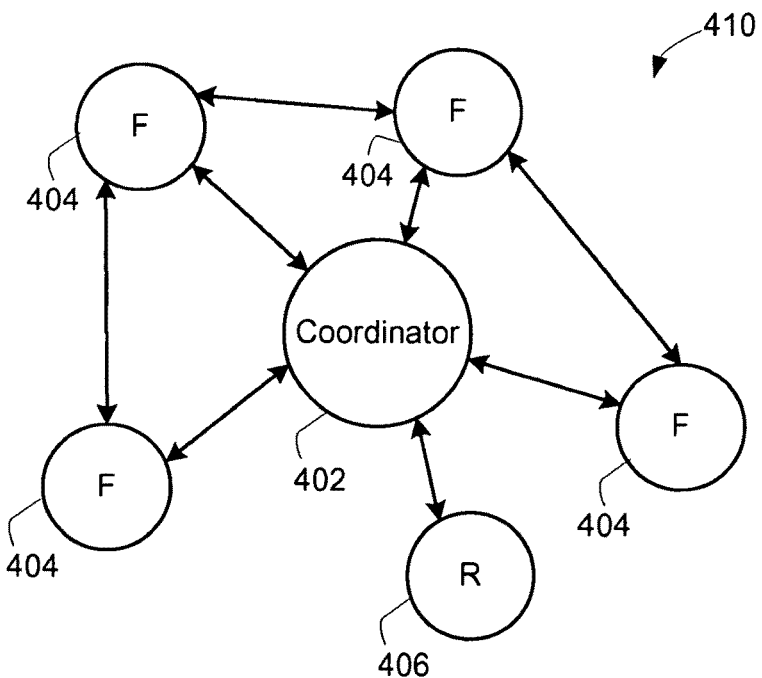

FIGS. 4A and 4B are block diagrams of wireless networks 400 and 410 for microwave tomography according to example embodiments. Wireless network 400 represents a star network example, while wireless network 410 represents a peer to peer network. The wireless networks 400 and 410 include a coordinator 402, FFDs 404 and RFDs 406.

In the star network, a single, central controller talks with all devices 404 and 406 of the wireless network 400 directly. All of the other devices 404 and 406 are only allowed to communicate with other nodes via the coordinator 402. All messages passed in the star network may be required to go through the coordinator 402.

The peer to peer network also may have a single coordinator 402; however, FFDs 404 are allowed to communicate amongst themselves without routing messages through the coordinator 402. This allows for more complex network setups where multiple hops can be used to deliver messages among nodes more efficiently.

By collecting RSSI information from several RFDs 406 lined up opposite of a coordinator 402, several tomographic projections may be taken. Gathering information from the projections permit piecing together what and where physical objects may be present within the boundaries of the network.

Figure 5:
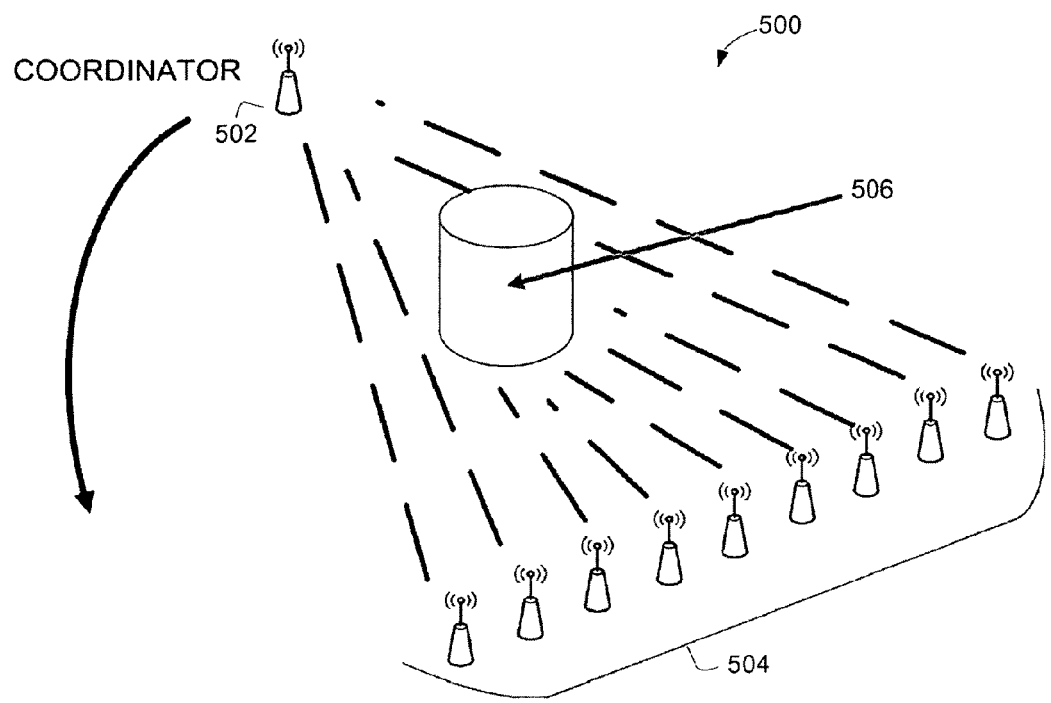
FIG. 5 is a diagram of an example single projection system according to an embodiment.

FIG. 5 is a diagram of an example single projection system 500 according to an embodiment. The single projection system 500 includes a coordinator 502, wireless devices 504 and a physical object 506.

Multiple projections are collected by either by having multiple wireless devices 504 present around the coordinator 502, or by moving the wireless devices 504 around the coordinator in spaced increments. This implementation allows for the coordinator 502 to receive varying RSSI values across multiple wireless paths. With the RSSI values and the path data, location information regarding the physical object 506 may be calculated. According to various embodiments, the coordinator 502 may collect and format the RSSI values along with other source identifying data to be communicated to an external computer or processor for tomographic processing.

Figure 6:
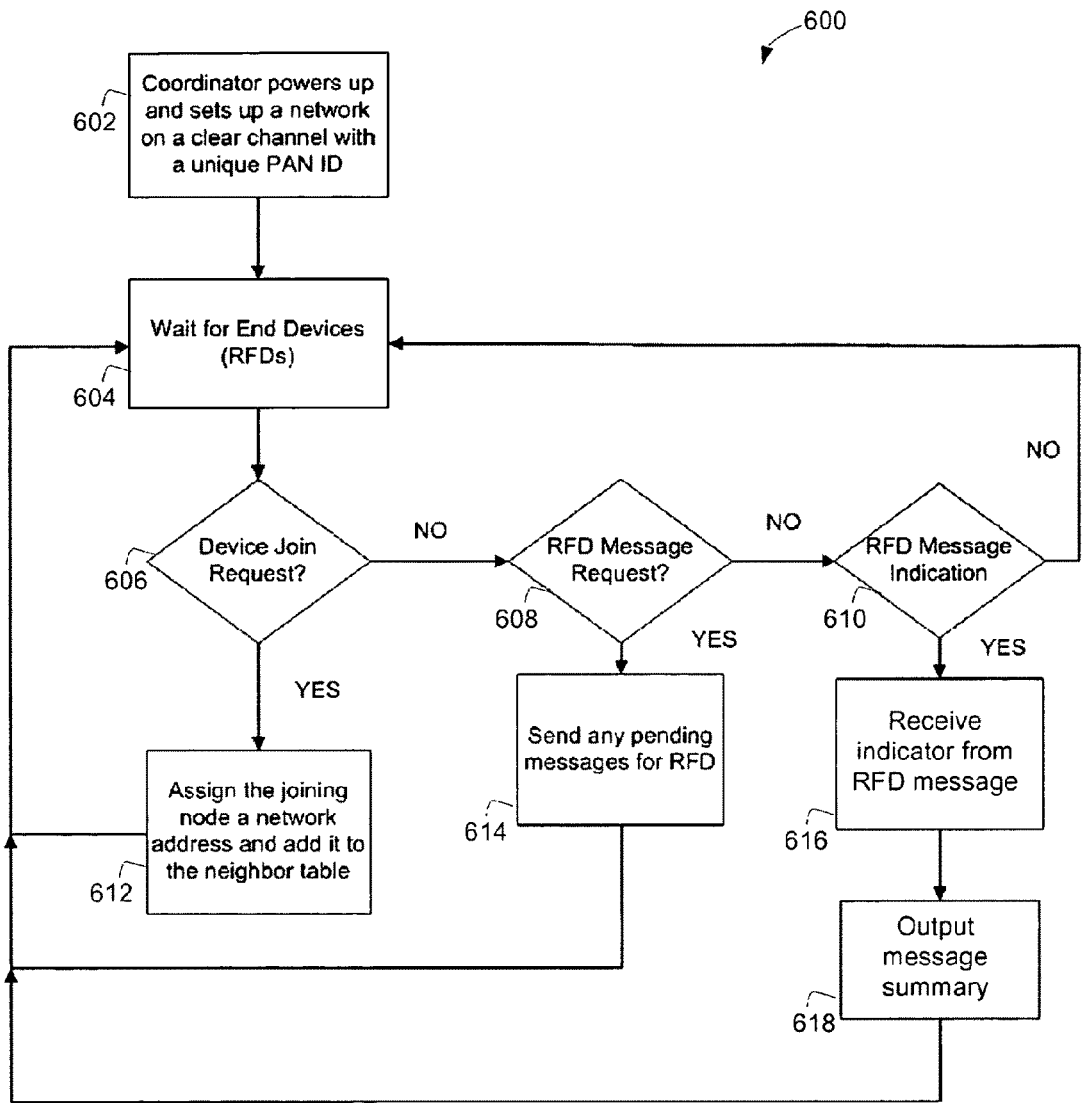
FIG. 6 is a flow diagram of a process for controller operation according to example embodiments.

FIG. 6 is a flow diagram of a process 600 for controller operation according to example embodiments. The process 600 starts with a coordinator powering up and setting up a network (block 602). The network may be set up on a clear channel using a unique ID. In an example embodiment, the unique ID may be a PAN ID where the coordinator is operating on a PAN. The coordinator may wait for remote devices to request to join the network (block 604). The coordinator may receive data packets from remote devices. As the data packets arrive, the coordinator may determine if the packet includes a join request (block 606). If the packet from a remote device includes a join request, the coordinator may assign the remote device a network address, and may also add that address to a neighbor table (block 612).

If the packet received by the coordinator does not include a join request, the coordinator may determine whether the packet includes a message request (block 608). If the packet includes a message request, the coordinator may then send any pending messages for the remote device (block 614). If the received packet does not include a message request, the coordinator may determine if the packet includes a message indication (block 610). If the packet does include a message indication, the coordinator may then receive the indicator from the message (block 616). The indicator may be RSSI, LQI, another similar indicator or a combination thereof. Upon receiving indicator, the coordinator may output a message summary (block 618). The output message summary may be analyzed and included in the production of a tomogram.

Figure 7:
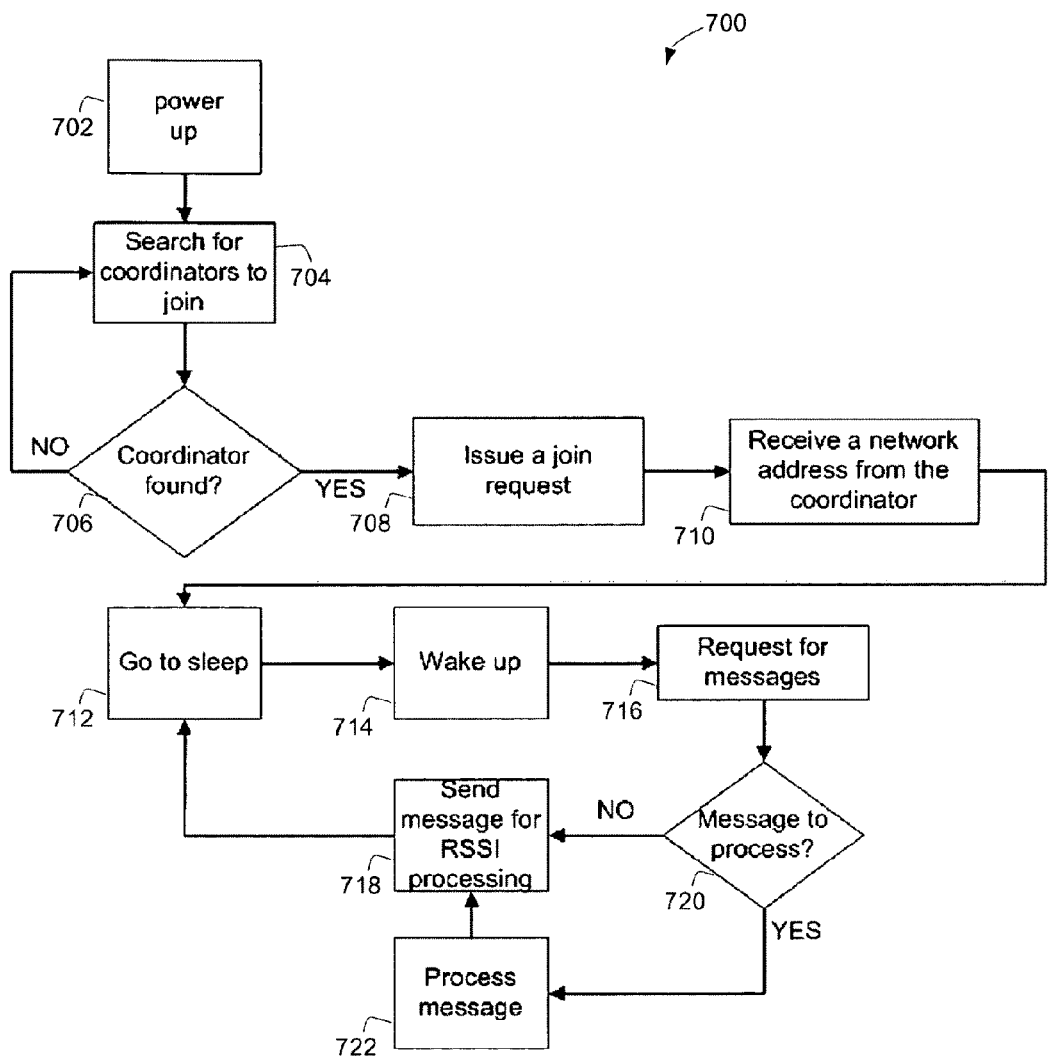
FIG. 7 is a flow diagram of a process for remote device operation according to example embodiments.

FIG. 7 is a flow diagram of a process 700 for remote device operation according to example embodiments. The process 700 may start with a remote device powering up (block 702) and searching for coordinators with which to join and network (block 704). If no coordinator is found (block 706), the remote device may continue searching for coordinators (block 704). Once a coordinator is found, the remote device may issue a join request (block 708). Upon being allowed to join with a coordinator, the remote device may receive a network address from the coordinator (block 710). The remote device may enter a sleep or idle mode once networked (block 712). The remote device may enter this idle state where it goes to sleep and occasionally checks for messages from the coordinator. Once awake, the remote device may start transmitting packets to the coordinator. In an example embodiment, the remote device may continue to transmit packets at a predetermined rate, possibly on the order of once every 0.5 seconds until it is powered down or reset.

Upon waking (block 714), the remote device may transmit a request for messages to the coordinator (block 716). If there is a message to process (block 720), the remote device may process the message (block 722), and then send a message for indicator processing (block 718). The indicator may be RSSI or LQI for example. If there is no message to process from the coordinator (block 720), the remote device may also send a message for indicator processing (block 718).

Figure 8:
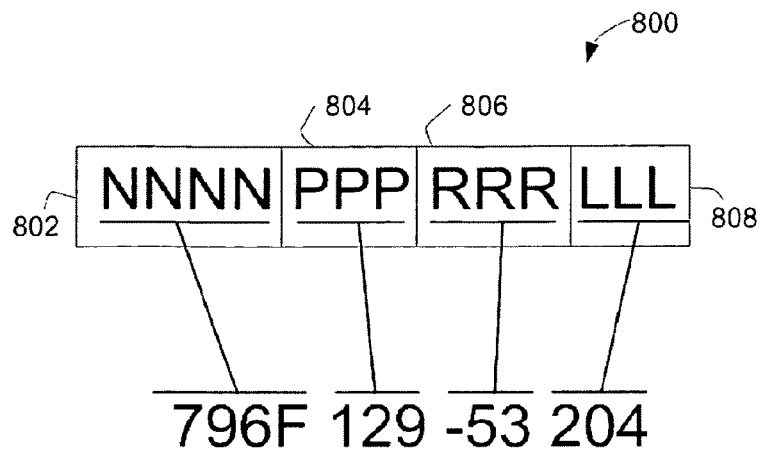
FIG. 8 is a diagram of coordinator data output according to example embodiments.

FIG. 8 is a diagram of coordinator data output 800 according to example embodiments. The data output 800 includes a source node address 802, a packet identification ("ID") 804, a RSSI value 806 and a LQI value 808.

A coordinator may receive packets from remote devices as source nodes. The payload of the packets transmitted is not a concern as the source node address 802, packet ID 804, RSSI value 806, and LQI value 808 are of interest. These variables may be found in the PHY and MAC layers. Each remote device may fill the payload with data of some sort, whether it is a regular transmission or dummy data. The remote device may address the packets to an endpoint on the coordinator. The endpoint on the coordinator may make function calls on the stack to retrieve the variables of interest from the lower levels of the stack regarding the message received.

The coordinator may then report that it received a message in the format of the data output 800. As an example configuration, "NNNN" is a short address 802 of the associated source node in hex (two bytes), PPP is the packet ID 804 number from the source node, RRR is the RSSI value 806 for that particular packet, and LLL is the LQI value 808 of the packet received. The LQI data may be merely collected at this point and may not necessarily be used in the creation of tomographic images. The example in FIG. 8 shows that node 796F sent packet ID 129 with an RSSI value of −53 dBm and LQI value of 204.

Figure 9:
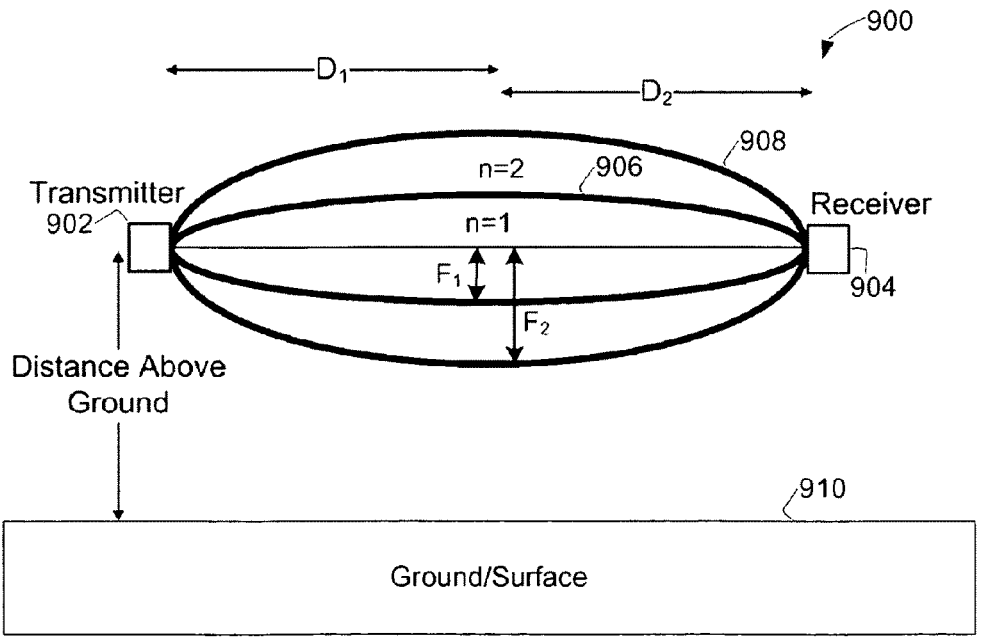
FIG. 9 is a block diagram of a Fresnel zone according to various embodiments.

FIG. 9 is a block diagram of Fresnel zones 900 according to various embodiments. FIG. 9 includes a transmitter 902, a receiver 904, a first Fresnel zone $F_1$ 906, a second Fresnel zone $F_2$ 908 and a surface 910. Determining the placement of nodes with respect to known obstacles or surfaces 910 such as the ground may be useful in accurately measuring signal strength. Appropriate clearance may assure that the RSSI value reported by a coordinator is not stronger or weaker that the straight-line path signal strength. By calculating the Fresnel zone distances 906 and 908, sufficient clearance of obstacles and surfaces for any two nodes participating in the network may be determined. The Fresnel zone expression for this geometry is:

$$F_n = \sqrt{\frac{n\lambda D_1 D_2}{D_1 + D_2}}.$$

From this expression, example Fresnel Zone calculations may produce $F_1$=0.3904 m, and $F_2$=0.5521 m. Since the strongest signals lie within the first two Fresnel zones 906 and 908, we need only be concerned with interference from multipath along these. To stay clear of the second Fresnel zone, a distance of 0.5521 meters minimum must be clear. Using these numbers, placing the nodes at a height of above 0.5521 meters above the surface 910 they will be clear of any noticeable multipath due to ground reflection.

Figure 10:
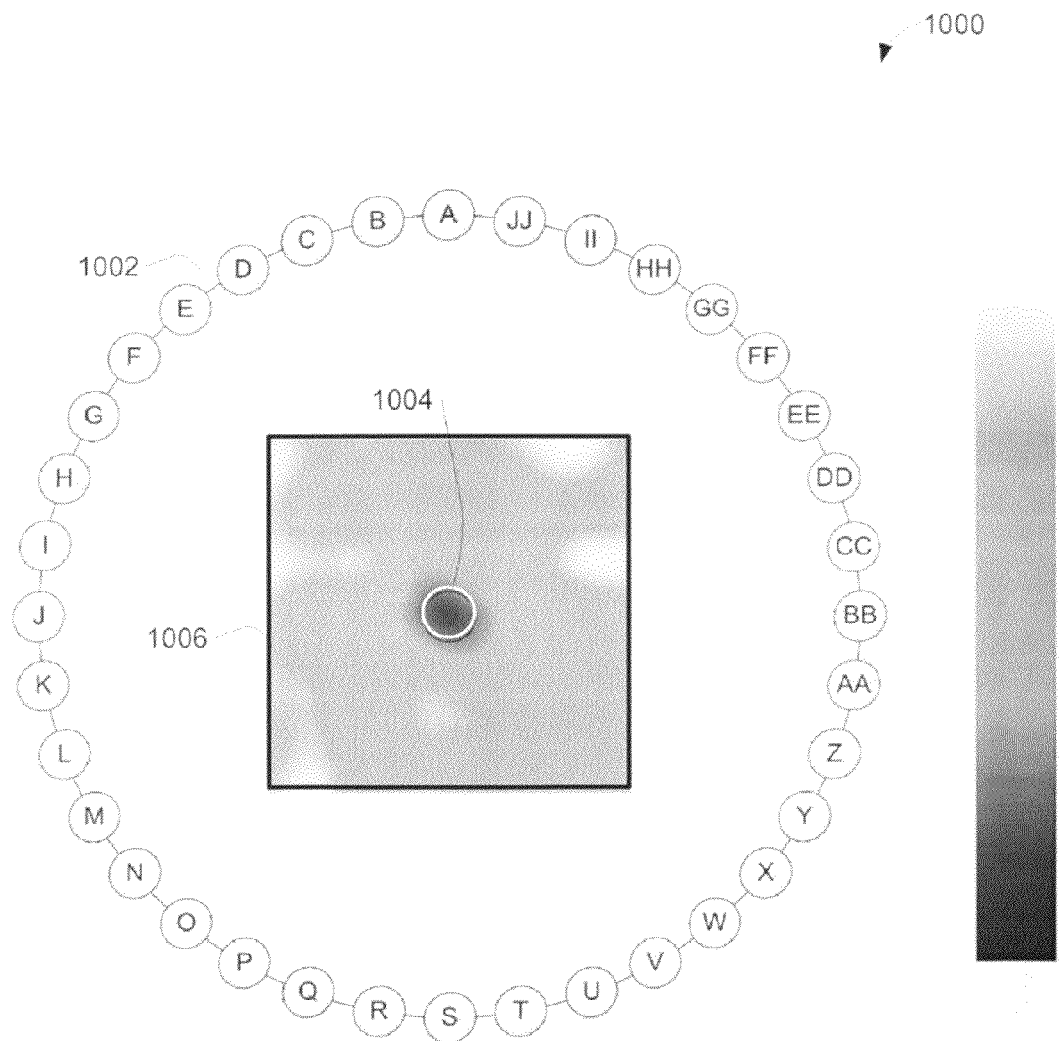
FIG. 10 is a diagram of example of a multiple projection system according to an embodiment.

FIG. 10 is a diagram of example of a multiple projection system 1000 according to an embodiment. The system 1000 includes multiple projection points 1002, an output image 1006 and a phantom 1004. The projection points 1002 may include a number of points in a rotation around a physical object. In an example, 36 projection points 1002 may be used at 10 degrees of rotation each. Remote devices may be arranged upon one or more of the projection points 1002, with coordinators generally arranged opposite each remote device. Wireless transmissions or projections between the remote devices and the coordinators may then be used to determine the presence of a physical object within the network boundary. The capture of RSSI data from any one projection may be averaged. Once all the data is gathered, the data may be inverted using computed tomographic algorithms to generate an output image 1006 or images of the physical space the network covers. Within an output image 1006, a phantom 1004 may exist identifying a physical object within the network boundary.

In an example embodiment, using 802.15.4/ZigBee technology, Microchip PICDEM Z boards may be used. The PICDEM Z supports a 28- or 40-pin DIP microcontroller. A list of built-in peripherals include a $R^S$-232 DB-9 connector, three momentary push buttons, LEDs, an in circuit serial programmer (ICSP), 9V battery clip, and an external power supply jack.

Ten PICDEM Z nodes may be utilized for a test conducted to take advantage of their pre-packaged 802.15.4 ready radio and software stack. Nine may serve as RFDs and one as the coordinator in a star topology network. There are several components to the PICDEM Z boards, including the wireless nodes themselves. The radio for each node is a Chipcon CC2420, ZigBee-certified transceiver which is integrated on a printed circuit board (PCB) with an inverted F-type PCB antenna.

The motherboards that the radios connect to are run with a Microchip PIC18LF4620 microcontroller that is clocked at 4 MHz. The controller effectively runs at 16 MHz after the 4× phase-locked loop (PLL) is engaged. This may be the highest speed possible with the oscillator included on each PICDEM Z board. The motherboard provides power to everything with a 9V DC to 3.3V DC voltage regulator rated at 100 mA.

The PICDEM Z boards also provide a RJ-11 connection for Microchip's in-circuit debugger (ICD2) so that projects created in MPLAB IDE can easily be programmed onto he microcontroller in a matter of seconds. This also frees the application developer from having to remove the microcontroller from the PICDEM Z every time a node's firmware needs to be updated.

Code for the microcontroller may be written using the MPLAB Integrated Development Environment (IDE). The IDE also provides a software interface with an ICD2 device which connects to a PICDEM Z board.

The ZigBee software stack uses the Microchip's C18 compiler to create a hex file that is programmed onto the microcontroller. Note that compiler optimizations should to be enabled so that the Coordinator code can fit onto the microcontroller.

Microchip provides a software stack of the ZigBee protocol which is designed to run on most of Microchip's 18F series microcontrollers and is written in the C programming language.

When the appropriate files from the stack are included, a programmer may focus on the application layer file which makes calls on the ZigBee protocol functions. The stack may handle everything except primitives that come back to the application-level in which code may be used to handle those primitives.

The PIC18LF4620 is a 40-pin DIP package microcontroller produced by Microchip. It is nearly identical to the PIC18F4620 other than this microcontroller has had its integrated electronics designed to operate over the range of 2.0V to 5.5V rather than 4.2V to 5.5V to reduce power consumption. Key characteristics include 64Kbytes of Flash program memory and 3986 bytes of data memory. There are four timers, one 8-bit timer (TMR2) and 3 16-it timers (TMR0, TMR1, TMR3). The stack uses TMR0, while the other timers are free.

The CC2420 is an IEEE 802.15.4 compliant RF transceiver manufactured by Chipcon/TI and is the radio used with the PICDEM Z boards. The CC2420 can be found on a daughterboard manufactured by Microchip which plugs into the motherboard with the microcontroller. The communication between the CC2420 and PIC18LF4620 may be done using 4-wire serial peripheral interface (SPI) (SDO, SDI, SCLK, CSn). In this configuration, the CC2420 acts as a slave and the PIC18LF4620 is the master. The CC2420 is suitable for both RFD and FFD operation since the determination of what role each node plays is in the code on the microcontroller. The CC2420 RF output power is controllable with a register named TXCTRL.PA_LEVEL. There are eight levels of output power ranging from 0 dBm to −25 dBm.

The CC2420 provides 8-bit resolution of the RSSI value. The digital value is in 2's complement (−128 to +127) and has a dynamic range of approximately 100 dB from 0 dBm to −100 dBm. The accuracy of the RSSI value is +/−6 dB. The raw RSSI value given by the CC2420 then needs to have an offset value added to the raw RSSI value to obtain actual RF input power. In an embodiment, −45 as the offset may be used to add to this value to obtain the actual RSSI. For example, if the value read from the CC2420 is −20, the RF input power is then calculated to be −65 dBm.

A frame check sequence (FCS) may be automatically generated and verified by the hardware onboard the CC2420. An option exists to disable the automatic detection and the cyclic redundancy check (CRC) would then need to be performed on the microcontroller firmware using the FCS polynomial stated by the IEEE 802.15.4 standard. For this example, the default option of having the FCS checked by the CC2420 is chosen to free up resources on the microcontroller.

The CC420 also has the capability to be used as not only a DSSS radio, but a Frequency Hopping Spread Spectrum (FHSS). The trade-off is a system that is not 802.15.4 compliant and a MAC layer that would need to be customized so that all the radios are synchronized to operating on the same channel at the same time.

Using MPLAB and the ZigBee stack, a straight forward application may be developed. With reference to FIGS. 6 and 7, a coordinator first establishes a network on a clear channel. Afterwards, each RFD can be activated and automatically search for and connect to the coordinator. At this point the coordinator may assign a 16-bit network (NWK) address to the joining node. In an example, in order to decrease network formation and discovery time, every node may be forced to work on channel 15 and transmit at full power (0 dBm).

The RFD may enter an idle state where it goes to sleep and occasionally checks for messages from the coordinator. Once a button on the RFD motherboard is pressed, an external interrupt is triggered and sets a flag to let the RFD know it is time to start transmitting packets to the coordinator. The RFD will continue to transmit packets at a pre-determined rate, currently set at once every 0.5 seconds until it is powered down or reset. This is done by using TMR1 on the PIC18LF4620 and counting the number of times it interrupts which equates to 0.5 seconds at the operating clock frequency.

A computer connected to the coordinator may be equipped with a graphical user interface (GUI) that was written to interface with the described system. The GUI may provide tomographic imagery from stored data or in real time illustrating measured areas of the network. The GUI may also provide a means of quickly analyzing and troubleshooting the network for data anomalies and connectivity of the nodes. There may also be a means for recording data to a file while running tests.

The GUI may include several text fields and bar graphs. Each bar graph corresponds to an RFD in the network that is connected to the coordinator. If an RFD is transmitting packets, the RSSI value received from the RFD is reported to the GUI and displayed graphically. Timers are used to keep track of how recently a packet has been received from a node. If an extended period of time has passed (set at 2.0 seconds) since an RFD last sent a packet, the GUI may display "- - - -" for that particular RFD and clear it's RSSI bar graph. This allows quick determination of what nodes are connected and actively transmitting to the coordinator.

One button on the GUI may allow a user to take samples of the RSSI data from all of the transmitting nodes and average the RSSI value seen over the next 16 transmissions from each RFD. This feature may help calibrate each RFD and provide a way to graphically display the RSSI in an intuitive fashion.

Another button located on the GUI enables a user to collect data from the time the button is first clicked to when it is clicked again. All of the raw data sent to the GUI from the coordinator can then be saved as a .txt file on the computer that the GUI is running. In addition to the raw data that is saved, if samples had been taken for the configuration, the averages are saved at the top of the file. This feature provides a method of preserving the data for future analysis.

The methods and systems described herein may additionally include additional nodes, varying frequencies of wireless transmission, varying positioning of nodes with respect to each other or objects, and varying power levels. The use of different antennas may also alter the accuracy of the devices. Reduced node size would allow for practical use in embedding at regular intervals in the walls of buildings where the power could then come from flat conductors within the wall.

The spatial resolution may be limited by the wavelength of the electromagnetic radiation used. This is approximately 12.5 cm with 802.15.4 technology. The actual spatial resolution of the system may also be affected by the number and spacing of the RFD nodes. Actual resolution can be increased by increasing the number of RFD nodes.

The imaging rate may be limited by the packet transmission rate of the network. Transmitting packets containing zero bytes in the payload of the packet (zero payload is the minimum packet size permitted by the standard), the minimum packet length required would be 16 bytes. Assuming use of the 802.15.4 specification's maximal data rate of 250 kbps, and assuming a 9 RFD node configuration (as an example implementation), it would be possible to acquire one image every 4.6 mS. Further reduction in the acquisition rate may be expected due to dropped packets, inter-nodal clock jitter, and other system nonidealities.

A non-linear configuration of the RFDs would utilize more robust tomographic algorithms, but provides for more flexibility in application uses. It may be possible to accurately recreate tomographic images with irregular geometries of sensors. The capability of deploying RFDs in non-uniform orientations is useful in many applications.

Wherever there is a wireless network, the framework is already in place to piggyback a tomographic application to gather cross-sectional data about objects that may lie within its boundary.

A possible life-saving application example, according to an embodiment, includes the use of the present subject matter in difficult to reach places of buildings, particularly skyscrapers. By embedding a compliant radio in the walls of each floor of the building at known locations, cross-sectional images of each floor of a building could be generated. During the event of an emergency, such as a fire or earthquake, the data from the network could be used to help rescuers determine where to focus their efforts. A wireless sensor network has the benefit of not being deterred by smoke and flames that IR sensors and video cameras would encounter.

The simplicity and power-saving properties of 802.15.4 may be implemented to pass periodic, small packets among nodes that are dispersed over large and remote areas, such as farm fields or forests. These nodes may also then be used to measure air moisture and precipitation that falls within a region by utilizing the tomography aspect of the microwaves in the network. The results from the tomography analysis could then be compared to radar and satellite estimates. This will allow meteorologist to improve their tools and predictions. The ability to measure rain over a large area rather than at discrete locations where rain gauges are located is a highly sought-after tool in hydrology.

Figure 11:
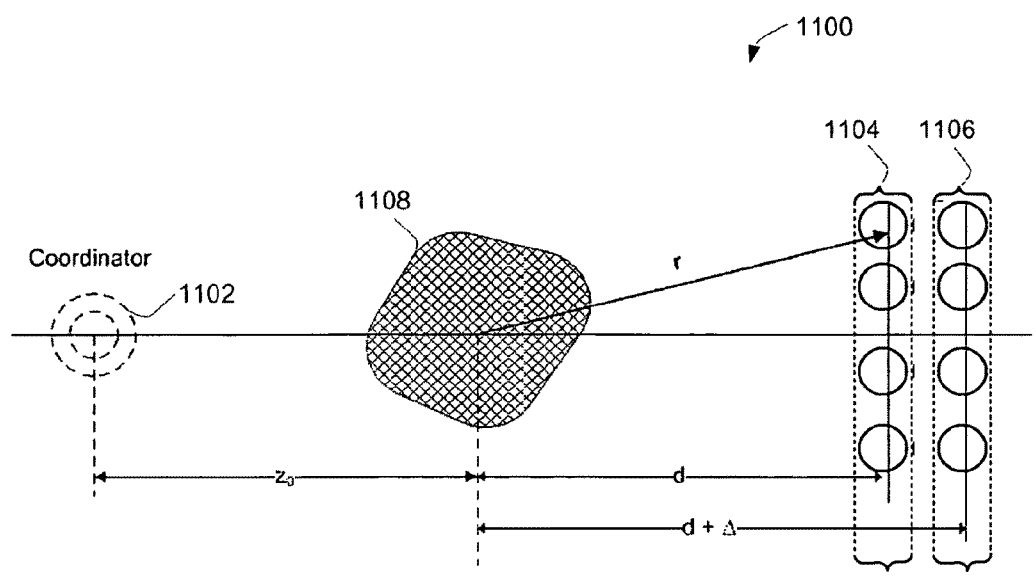
FIG. 11 is a diagram of a system using a phase data gathering configuration according to various embodiments.

FIG. 11 is a diagram of a system 1100 using a phase data gathering configuration according to various embodiments. The system 1100 includes a coordinator 1102, a first row or remote devices 1104, a second row of remote devices, and a microwave diffracting object 1108. Using diffraction tomography (DT) algorithms, phase, as well as signal intensity of transmitted packets among nodes (remote devices and coordinators) in the network may be needed. It is possible to obtain phase data in such a network using a second row of remote devices 1106 placed behind the first row of remote devices 1104 at a known distance, Δ. With two sets of intensity data and known distances for each projection calculating phase is possible.

Figure 12:
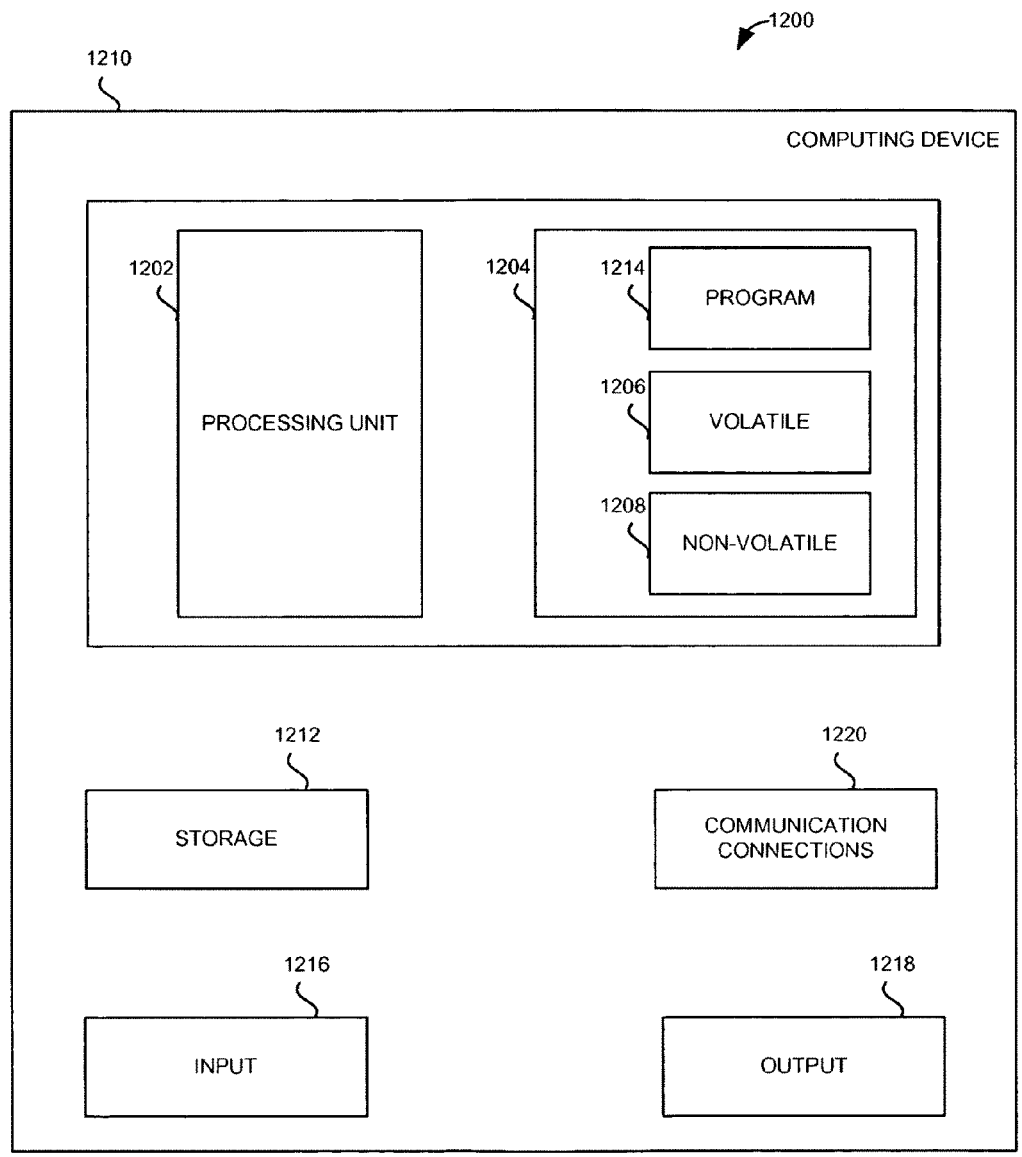
FIG. 12 illustrates a computer system that executes programming for microwave tomography according to various embodiments.

FIG. 12 illustrates a computer system that executes programming for microwave tomography according to various embodiments. A general computing device 1210 may include a processing unit 1202, memory 1204, and storage 1212. Computer-readable instructions stored on a computer-readable medium are executable by the processing unit 1202 of the computing device 1210. A hard drive, CD-ROM, and RAM are some examples of articles including a computer-readable medium. Instructions for implementing any of the above described methods and processes may be stored on any of the computer readable media for execution by the processing unit 1202. The memory 1204 may include volatile memory 1206 and/or non-volatile memory 1208. Additionally, the memory 1204 may include program data 1214 which may be used in the execution of various processes. Storage for the computing device may include random access memory (RAM), read only memory (ROM), erasable programmable read-only memory (EPROM) & electrically erasable programmable read-only memory (EEPROM), flash memory, one or more registers, or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions.

The computing device 1210 may include or have access to a computing environment that may include an input 1216, an output 1218, and communication connections 1220. The computing device 1210 may operate in a networked environment using a communication connection to connect to one or more other computing devices, processors or other circuits. In some embodiments, the computing device 1210 may determine signal strength or quality data from received wireless packets. The computing device 1210 may additionally determine tomographic information based on the signal strength or quality data from the received wireless packets.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

What is claimed is:

1. A method comprising:
receiving a packet wirelessly transmitted within a wireless data network from a first node to a second node, the packet including non-payload data including signal strength information and source location information;
analyzing a signal strength value of the received packet and a relative location of the first node using the non-payload data;
performing a tomographic analysis based on the signal strength value and the relative location of the first node, the tomographic analysis creating a tomographic image;
determining whether a physical object is present at least partially between the first node and the second node such that the packet is transmitted through the physical object using the tomographic image; and
outputting data based on the determination of the presence of the physical object.

2. The method of claim 1, wherein the packet is transmitted using a spread spectrum transmission.

3. The method of claim 1, wherein the wireless data network is a personal area network (PAN).

4. The method of claim 1, wherein the signal strength value is a received signal strength indication (RSSI) value.

5. The method of claim 1, further comprising receiving one or more further packets and measuring signal strength values of the received one or more further packets transmitted within the wireless data network.

6. The method of claim 5, further comprising determining size characteristics of the physical object based on the signal strength values of the received packet and the received one or more further packets.

7. The method of claim 5, further comprising determining position characteristics of the physical object based on the signal strength values of the received packet and the received one or more further packets.

8. The method of claim 5, further comprising determining shape characteristics of the physical object based on the signal strength values of the received packet and the received one or more further packets.

9. A system for determining presence of a physical object in a wireless network, the system comprising:
a wireless device of the wireless network, the wireless device including:
a receiver configured to receive a packet transmitted from a transmitter of the wireless network over a wireless path being a straight-line path between the transmitter and the receiver in the wireless network; and a packet analysis module configured to collect non-payload data from the received packet, the non-payload data including information on signal strength and relative location of the transmitter; and an external device configured to communicate with the wireless device, wherein one of the packet analysis module and the external device is configured to perform a tomographic analysis creating a tomographic image using the information on signal strength and relative location of the transmitter and determine the presence of the physical object along the wireless path using the tomographic image.

10. The system of claim 9, wherein the non-payload data includes link quality data.

11. The system of claim 9, wherein the packet analysis module is configured to communicate the non-payload data to the external processor, and the external processor is configured to determine the presence of the physical object along the wireless path using the information on signal strength and relative location of the transmitter by performing the tomographic analysis based on the non-payload data.

12. The system of claim 9, further comprising a transmitter configured to transmit a packet over a wireless path, the packet including an identification associated with the receiver, and signal strength data.

13. A system for determining presence of a physical object in a wireless network, the system comprising:

a first device of the wireless network, the first device configured to transmit a packet over a wireless medium, the packet including non-payload data including signal strength information and source location information indicative of location of the first device;

a second device of the wireless network, the second device configured to receive the packet; and an analysis module in communication with the second device, the analysis module configured to perform a tomographic analysis creating a tomographic image using the non-payload data including the signal strength information and the source location information and determine presence of the physical object at least partially along a straight-line path between the first device and the second device using the tomographic image.

14. The system of claim 13, further comprising:

a third device configured to transmit a further packet over the wireless medium; and a fourth device configured to receive the further packet, wherein the analysis module is in communication with the fourth device and configured to analyze non-payload data of the received further packet in the tomographic analysis to determine the location of the physical object within the wireless network.

15. A system for determining presence of a physical object in a wireless network, the system comprising:

a packet analysis module configured to interface with a wireless receiver of the wireless network and analyze non-payload information of packets received by the wireless receiver, the packets transmitted from a wireless transmitter of the wireless network to the wireless receiver through a straight-line path between the wireless transmitter and the wireless receiver, the non-payload information including signal strength information and source location information allowing for determination of a location of the wireless transmitter, the packet analysis module configured to output the analyzed non-payload information; and a data analysis application configured to receive the analyzed non-payload information from the packet analysis module, perform a tomographic analysis creating a tomographic image using the analyzed non-payload information including the location of the wireless transmitter, and calculate physical characteristics of the physical object within a wireless network using the tomographic image, the physical object being substantially along the straight-line path between the wireless transmitter and the wireless receiver.

16. The system of claim 15, wherein the physical characteristics of the physical object include at least one of the following: location, size, shape, reflectivity, and motion.

17. The system of claim 15, further comprising an interface displaying the location of the physical object within the wireless network.

18. The system of claim 15 further comprising at least one additional packet analysis module to interface with one or more additional wireless receivers to analyze non-payload information of additional packets received by the additional wireless receivers, and to output the non-payload information of the additional packets to the data analysis application.

19. The system of claim 15, wherein the data analysis application is physically separate from the packet analysis module.

* * * * *

UNITED STATES PATENT AND TRADEMARK OFFICE
CERTIFICATE OF CORRECTION

PATENT NO. : 8,526,341 B2
APPLICATION NO. : 12/123346
DATED : September 3, 2013
INVENTOR(S) : Cover et al.

It is certified that error appears in the above-identified patent and that said Letters Patent is hereby corrected as shown below:

In the Specification

In column 3, line 46, delete "(LR_WPANs)" and insert --(LR_WPANs)).--, therefor

In column 5, line 13, delete "predetermined" and insert --pre-determined--, therefor In column 6, line 31, delete "$R^S$" and insert --RS--, therefor In column 7, line 18, delete "3 16-it" and insert --three 16-bit--, therefor In column 9, line 39, delete "or" and insert --of--, therefor In column 9, line 40, after "devices", insert --1106--, therefor Signed and Sealed this
Twentieth Day of May, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,526,341 B2
APPLICATION NO. : 12/123346
DATED : September 3, 2013
INVENTOR(S) : Cover et al.

Page 1 of 1

It is certified that error appears in the above-identified patent and that said Letters Patent is hereby corrected as shown below:

In the Specification

In Column 1, Lines 11-14, delete "This invention was made with a grant from the Government of the United States of America (Grant No. DK64659 from The National Institutes of Health). The Government has certain rights in the invention." and insert --This invention was made with government support under DK064659 awarded by the National Institutes of Health. The government has certain rights in this invention.-- therefor Signed and Sealed this
Fourteenth Day of January, 2025

Derrick Brent
*Acting Director of the United States Patent and Trademark Office*